Figure 1:
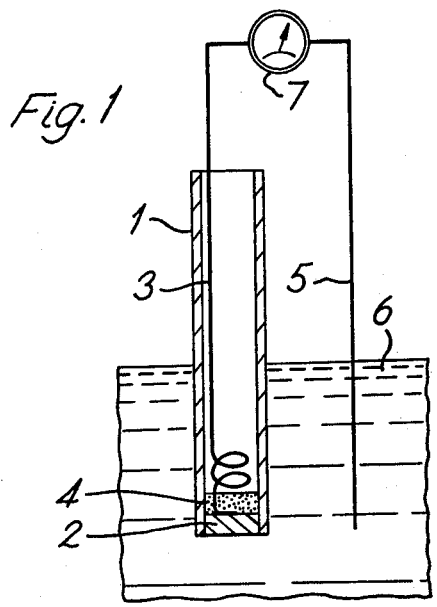

United States Patent [19]

Fray

[11] 4,085,023

[45] Apr. 18, 1978

[54] APPARATUS FOR DETECTING ELEMENTS

[75] Inventor: Derek John Fray, Haslingfield, England

[73] Assignee: National Research Development Corporation, London, England

[21] Appl. No.: 592,200

[22] Filed: Jul. 1, 1975

[30] Foreign Application Priority Data

Jul. 3, 1974 United Kingdom ............... 29490/74

[51] Int. Cl.² ........................................... G01N 27/46
[52] U.S. Cl. ................................. 204/195 S; 204/1 T; 429/33; 429/104; 429/193
[58] Field of Search ........................... 136/6 FS, 83 R; 204/1 S, 195 S; 429/104, 193, 33

[56] References Cited

U.S. PATENT DOCUMENTS

| | | | |
|---|---|---|---|
| 3,297,551 | 1/1967 | Alcock | 204/195 S |
| 3,404,036 | 10/1968 | Kummer et al. | 136/6 FS |
| 3,535,163 | 10/1970 | Dzieciuch et al. | 136/6 FS |
| 3,619,381 | 11/1971 | Fitterer | 204/195 S |
| 3,895,963 | 7/1975 | McGowan et al. | 136/6 FS |
| 3,918,991 | 11/1975 | Hess | 136/83 R |
| 3,977,899 | 8/1976 | Takeda | 429/193 |

*Primary Examiner*—T. Tung
*Attorney, Agent, or Firm*—Cushman, Darby & Cushman

[57] ABSTRACT

A method and apparatus for the detection or determination of an element in a substance comprising that element by monitoring the e.m.f. generated between the substance and a reference material, in which the reference material is a solid compound of said element separated from the substance by said electrolyte.

14 Claims, 2 Drawing Figures

APPARATUS FOR DETECTING ELEMENTS

The present invention relates to the detection and determination of small quantities of single elements normally in the presence of other materials, and in particular to the detection and determination of impurities of specific elements in solid or molten metal or alloys.

There are numerous industrial applications where it is advantageous to be able to measure simply and quickly the levels of such impurities. For example, in the field of metallurgical refining it is often desirable to estimate impurities whilst the metal is still in the molten state so that the composition may be adjusted before it is cast.

A galvanic method for determining the sodium activity in molten metal has been proposed using a probe based on a sodium β-alumina solid electrolyte (Smeltzer et al, Canadian Metallurgical Quarterly Vol. 12 No. 2 (1973) pages 155–158). The probe consists of a pellet of sodium β-alumina sealed with Kovar 7052 glass to an α-alumina tube containing a molten metallic sodium reference. This probe was used to determine the amount of sodium present in molten tin at 500° C, but failed at this temperature after 4 hours due to break down of the glass seal as a result of attack from the molten sodium reference. This failure of the probe renders it unsuitable for use in industrial applications, such as aluminium refining, where the temperatures to be withstood are much higher e.g. 750°–800° C, and more particularly where the risk of contamination of the metal with sodium escaping from the reference cannot be tolerated, not withstanding the severe hazards incurred when sodium is heated to such elevated temperatures. An industrially applicable β-alumina probe has now been constructed.

According to the present invention there is provided a method for the detection or determination of an element in a substance comprising that element by monitoring the e.m.f. generated between the substance and a reference material, in which the reference material is a powdered solid compound of said element separated from the substance by an electrolyte in pellet form comprising a β-alumina containing said element.

The invention also includes within its scope an apparatus for carrying out the method of the invention.

Accordingly, the invention includes an apparatus for use in the detection or determination of an element in a substance comprising said element by monitoring the e.m.f. generated between the substance and a reference material, in which the reference material is a powdered solid compound of said element separated from the substance by an electrolyte in pellet form comprising a β-alumina containing said element.

The method and apparatus of the present invention may be utilised for the detection or determination of small quantities of single elements in a wide range of situations. For example, the element may be present as a component in the vapour or solid phase. More usually, however, the substance comprising the element is in the liquid or molten state, and the invention is particularly applicable to the detection or determination of impurities in molten metals or alloys.

The elements which may be detected or determined by the present invention are typically those which form β-aluminas. Examples of such elements are lithium, sodium, potassium, rubidium, copper, silver, thallium, indium and gallium, the various β-aluminas having a structure similar to that of sodium β-alumina with the element in question substituting for sodium.

Particular attention is paid in the present specification to the detection and determination of sodium, especially in the context of the production of aluminium and aluminium alloys, but it will be appreciated that the invention extends to other elements and other environments.

The composition of the β-alumina of the solid electrolyte pellet of the present invention may vary widely, though when the element in question is sodium the composition is typically in the range from $Na_2O.5Al_2O_3$ to $Na_2O.11Al_2O_3$, and β-aluminas of other elements e.g. Li, Na, K, Rb, Cu, Ag, Tl, In and Ga, are believed to have similar compositions. It has been found in practice, during the determination of sodium in molten aluminium, that when the β-alumina electrolyte contains a high proportion of the element, i.e. towards the composition given by the formula $Na_2O.5Al_2O_3$, discolouration and contamination of the electrolyte may occur during use. Thus in a preferred embodiment the electrolyte phase also contains a small amount of α-alumina, for instance a mixture of α-alumina and sodium β-alumina in which the ratio of $Al_2O_3$ to $Na_2O$ is in the range from 11:1 up to about 12:1 or more.

The reference material may be an electrically non-conducting material, though is preferably an electrically conducting material, either an electronic or an ionic conductor. Examples of suitable reference materials are stable salts of the elements being detected e.g. tungstates, molybdates and vanadates, and advantageously the reference material consists of a 2 phase material. Preferably, there is a separate reference material which comprises a β-alumina containing the element which is being determined, and is usually in the form of a two-phase material, for instance two-phase β-alumina, i.e. a mixture of β and β"-alumina, or a mixture of β and α-alumina.

It will be appreciated, however, that the activity of the element in the β-alumina reference e.g. the sodium in sodium β-alumina, is dependent to a certain extent upon the oxygen potential of the atmosphere over the reference material. Hence preferably the β-alumina reference material is maintained in an atmosphere having a fixed oxygen partial pressure, for instance in air under normal atmospheric conditions.

Typically the apparatus is in the form of a probe consisting at least in part of a β-alumina of the element which is being determined, and usually the e.m.f. which is monitored is generated between a pair of electrodes. The probe may be in any convenient form such as a body comprising β-alumina so shaped such that when in use the electrode which connects with the reference material or the β-alumina electrolyte is maintained out of physical contact with the substance containing the element which is being determined. A convenient form for the probe is a tube closed at one end. Thus in one embodiment the probe is in the form of a tube closed at one end consisting entirely of β-alumina, in which case one electrode may be secured directly to the tube for instance by means of a clip. It will be appreciated, however, that an additional e.m.f. may be generated in such a probe if there is a temperature gradient between the point of attachment of the electrode and the part of the probe which is contacted with the substance. Thus preferably the electrode is secured at a point adjacent to the part of the probe which contacts the substance.

It has been found however that when the probe is used in very high temperature environments such as in molten metals e.g. at temperatures of about 700° C or higher, the thermal shock experienced by the probe can cause it to break and fail. A design of probe which has been found to be particularly successful in overcoming this problem is in the form of a tube of a refractory material such as silicon nitride or preferably α-alumina, with a pellet comprising β-alumina sealing one end of the tube. A pellet having a diameter of from about ⅛ inch to about ¼ inch or especially about 3/16ths inch has been found to be satisfactory. The pellet may be sealed to the end of the tube by means of a sealing material. Preferably, however, the pellet is formed in situ in the end of the tube by hot pressing of powder comprising β-alumina, for instance at pressures ranging from about 20 up to about 100 Kg/cm$^2$ and temperatures ranging from about 1,000° up to 1,500° C. Particularly good results are achieved where both the pressure and the temperature are increased by steps or otherwise during the hot pressing, and furthermore when the pellet is subjected to a heat treatment after pressing.

In the usual arrangement when the probe is in the form of a tube sealed at one end by a pellet comprising β-alumina, there is an electrode which makes internal contact with the pellet. In a preferred embodiment the tube contains on top of the pellet a layer of powdered reference material which is either two-phase β-alumina or a mixture of β and α-alumina, and the internal electrode is pushed through the powder to make electrical contact with the pellet.

The apparatus is usually also provided with an external electrode, which when in use contacts the substance containing the element, and may take any suitable form. Conveniently both electrodes may be in the form of wires preferably of a metal which is sufficiently resistant to withstand the extreme temperature of molten metals e.g. stainless steel wires.

Generally when in use the external electrode and probe are contacted with the substance containing the element and the e.m.f. generated between the internal and external electrodes is monitored. The e.m.f. may be monitored by any suitable means though preferably a high impedance meter is employed. When the substance is a gas or a liquid such as a molten metal or alloy, the probe and external electrode are inserted into the gas or liquid. When the substance is a solid the probe and external electrode are contacted with the surface of the substance. In a preferred arrangement when the substance is a gas the external electrode contacts the β-alumina electrolyte at its external surface.

The use of the method and apparatus of the present invention leads to advantages in particular as a result of the very rapid e.m.f. response of the β-alumina probe. In some case the e.m.f. response of the probe may be practically instantaneous constituting a significant advantage over conventional glass electrodes which often take several minutes to equilibrate.

The present invention is particularly applicable to the determination and detection of small amounts of elements present in molten metals and alloys. For instance, there are many industrial processes where it is desirable to be able to determine small amounts of sodium present in molten metals or alloys, and some applications of the invention are as follows:

(A) MANUFACTURE OF TETRAETHYL LEAD

Tetraethyl lead is usually produced by reaction of ethyl chloride with a sodium/lead alloy. It has been found that an alloy of closely defined composition given by the formula Na.Pb is the easiest to handle and gives the highest yields of tetraethyl lead. Thus during production of this alloy it is desirable to be able to closely determine the sodium content.

(B) REMOVAL OF ARSENIC AND ANTIMONY FROM NON-FERROUS METALS

Impurities of arsenic and antimony which remain in some non-ferrous metals after primary reduction are usually removed by addition of sodium which forms stable arsenides and antimonides with these elements.

For example, the accepted technique in the zinc industry is to add the sodium in the form of sticks and to hold them beneath the liquid surface until reaction is complete. Often oxidation of the sodium takes place. Any additional sodium, above that required for arsenic removal, reacts with zinc to form a compound $NaZn_{13}$ with the result that approximately 50 lbs of zinc are combined with each additional pound of sodium. Additional wastage is caused when the so formed dross is removed; this inevitably results in entrapment of zinc, which all has to be reprocessed. In addition to combining with zinc to form a compound, there is solubility of sodium in zinc and this has the unfortunate effect of increasing the oxidation state of the zinc in all subsequent operations involving the material. Once again precise monitoring of the sodium content is of considerable importance.

For instance, in one method a sodium sensitive probe is inserted into the molten zinc and the e.m.f. is monitored throughout the addition of the sodium. When all the arsenic or antimony has reacted with the sodium, additional sodium alters the e.m.f. of the cell permitting far greater control than is exercised at present.

(C) MODIFICATION OF Al-Si ALLOYS

Silicon is often added to aluminium used for castings to increase its strength and wear resistance. However, cooling of the material must be very fast or the structure of the silicon in the aluminium-silicon eutectic is very coarse leading to a dull brittle alloy with poor mechanical properties. It has been found that addition of sodium to the metal prior to casting gives a much finer eutectic structure and a material with improved properties and casting behaviour. The levels of addition of sodium are quite critical, an excess of sodium causing over-modification which reduces the tensile values appreciably. For example, for an Al— 7.5% Si alloy the desired sodium content for modification is between 0.006% and 0.117% by weight. Hence it is advantageous to be able to measure the sodium content of this system, and in particular rapid determination is highly desirable as sodium vaporises quickly at the temperature of molten aluminium and the content is constantly changing. Thus again the present invention is particularly applicable in this case.

(D) ALUMINIUM PRODUCTION

When aluminium is tapped from the Hall cell it contains up to 0.1wt% sodium and, in order to eliminate the sodium the bath of molten aluminium is left to stand in the atmosphere allowing the sodium to evaporate. This leads to pollution of the atmosphere, energy is expended in maintaining the molten bath and also oxides form on the surface of the bath and some aluminium is lost when this oxide layer is removed. Thus it is desirable to be able to measure the sodium content so that pollution, energy loss and aluminium loss may be minimised.

Figure 2:
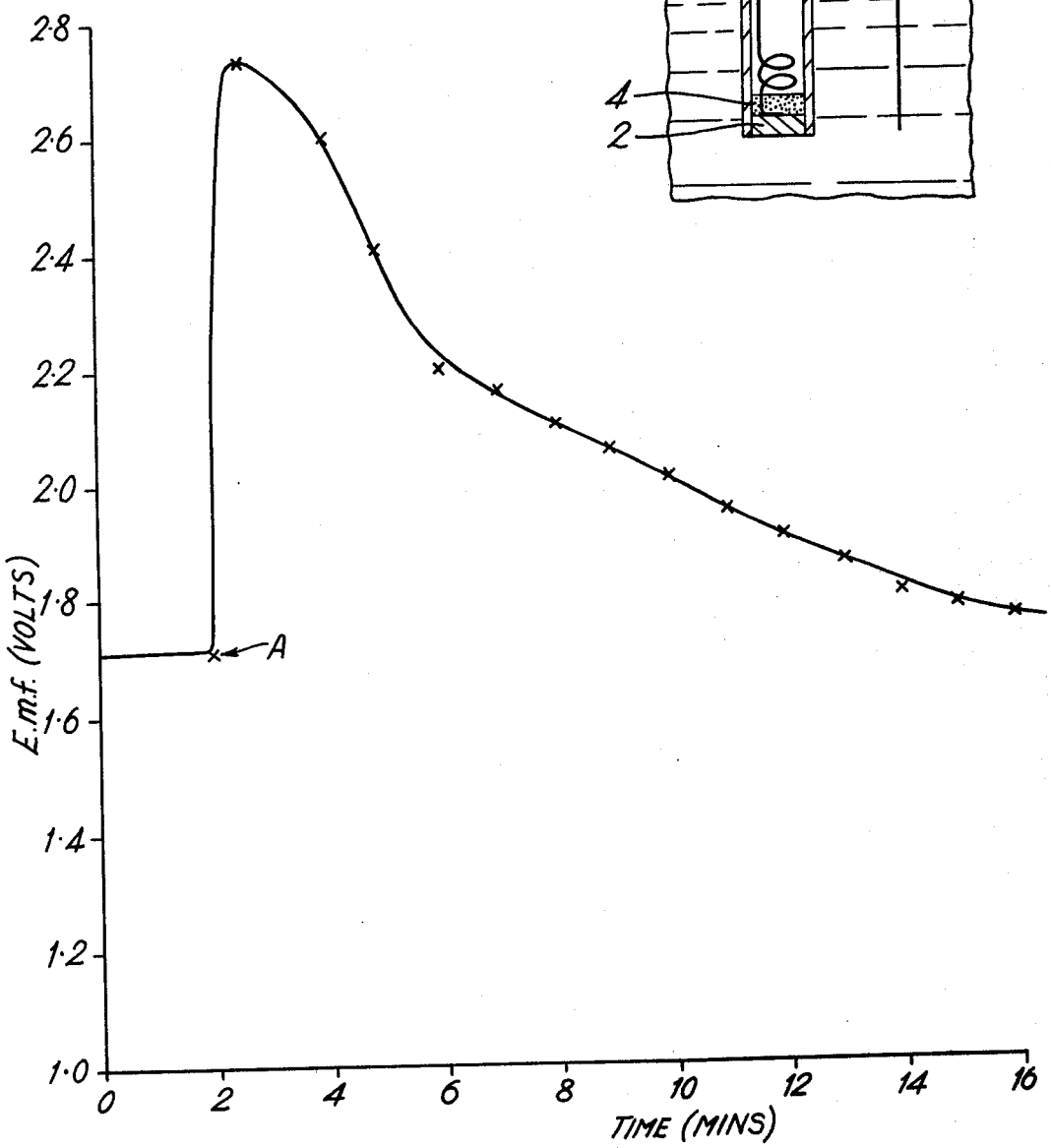

An apparatus and method according to the present invention will now be described by way of example with reference to the accompanying drawings in which:

FIG. 1 is a diagrammatic representation of a probe, for the detection or determination of sodium, constructed in accordance with the present invention, and FIG. 2 is a graph showing a typical curve of the e.m.f. of such a probe when inserted into a sodium containing molten Al-Si alloy, LM6.

The probe shown in FIG. 1 consists of an α-alumina tube 1 sealed at one end with a 3/16 inch diameter disc-shaped pellet 2 of sodium β-alumina containing excess α-alumina having approximately a composition in which the $Na_2O$ to $Al_2O_3$ ratio is approximately 1:12. The probe is provided with an internal reference electrode 3 in the form of a stainless steel wire which extends through a layer 4 of powdered two phase β-alumina reference material contacting the pellet 2 at its internal surface. The apparatus is also provided with an external electrode 5 in the form of a stainless steel wire. When in use the tube 1 together with the external electrode 5 are lowered into the substance 6, the sodium content of which is to be measured, and the e.m.f. which is generated virtually instantaneously between the internal 3 and external 5 electrodes is monitored using a suitable high impedance meter 7.

In the probe as above, the β-alumina pellet 2 is formed in situ in one end of the α-alumina tube 1 by a hot pressing technique. Sodium aluminate ($NaAl_2O_3$) and $α-Al_2O_3$ powder (both about 6μ in diameter) are well mixed and heated together in air at 1,400° C for 12 hours, after which the mixture is ground to a powder of diameter about 1μ in a ball-mill. 0.2 grams of the mixture, which consists of $Na_2O \cdot 11Al_2O_3$ with excess $α-Al_2O_3$, is placed in an $α-Al_2O_3$ tube 1 of internal diameter 3/16 inch held in a carbon block in a suitable hot pressing apparatus provided with a carbon rod of diameter 3/16 inch by means of which pressure may be applied to the powder. The powder is cold pressed at $25Kg/cm^2$ and the load is maintained whilst the apparatus is heated to a temperature of 1,150° C for 20 minutes. The load is then increased to $50Kg/cm^2$ and the temperature maintained at 1,150° C for 5 minutes, after which the temperature is increased to 1,400° C for a further five minutes. Heating is then discontinued and the system is cooled under pressure to room temperature. Most of the carbon rod is drilled out of the $α-Al_2O_3$ tube 1 and the remainder is burnt out using a small oxygen lance, the high temperatures reached during this burning operation helping to harden the pellet 2. By the above procedure a hard pellet 2 3/16 inch in diameter and about ⅛ inch thick is produced in one end of the $α-Al_2O_3$ tube 1 giving a gas-tight probe.

EXAMPLE 1

A probe and external electrode as described above are lowered into a crucible of molten aluminium-silicon alloy LM6 which has the composition:

| | |
|---|---|
| Si | 10-13% |
| Cu | 0.1% max. |
| Mg | 0.1% max. |
| Fe | 0.6% max. |
| Mn | 0.5% max. |
| Ni | 0.1% max. |
| Zn | 0.1% max. |
| Pb | 0.1% max. |
| Sn | 0.05% max. |
| Al | Balance |

The sodium is added to the molten alloy in the form of a flux and the e.m.f. generated between the internal and external electrodes is monitored. FIG. 2 shows a typical curve of the e.m.f. generated against time, the point A on the graph indicating the point at which the sodium is added. As can be seen the presence of the sodium in the alloy causes a sharp and instantaneous initial rise in the e.m.f. which then decays as the sodium is vaporised.

EXAMPLE 2

Similarly as in Example 1 the probe and external electrode are lowered into a crucible of molten aluminium-silicon alloy LM6 and sodium is added in the form of a flux. The e.m.f. generated between the internal and external electrodes is monitored and at a known voltage the alloy is sand cast. A sample of the sand cast alloy is analysed for sodium content by a combined vacuum distillation and atomic emission spectrometry technique. The procedure is repeated a number of times using different levels of sodium addition and the results obtained are given in Table I.

Table I

E.M.F. generated between the internal and external electrodes of a Na β-$Al_2O_3$ probe immersed in molten aluminium-silicon alloy LM6 containing various amounts of sodium

| E.M.F. generated in volts | wt% of Na in alloy |
|---|---|
| 1.75 | 0.003 |
| 1.90 | 0.006 |
| 2.1 | 0.0095 |
| 2.3 | 0.012 |
| 2.5 | 0.016 |

I claim:

1. An apparatus for use in the detection or determination of an element in a substance containing said element, comprising:

a voltmeter;

a substance-contactable electrode connected to one side of the voltmeter;

a reference electrode connected to the other side of the voltmeter;

a solid powdered reference material with which the reference electrode is in contact;

a tube containing the reference material, the tube being of a refractory material, a solid electrolyte pellet containing in and sealing one end of the tube, the pellet being exposed for contact with the sample substance, the pellet comprising a β-alumina containing the element to be determined or detected;

the reference material being a compound of said element to be determined or detected which compound is solid at 750° C. and is selected from the group consisting of two-phase β-alumina, a mixture of α-alumina and β-alumina, a tungstate, a molybdate and a vanadate, the tube being dippable into the substance containing said element to be detected or determined.

2. An apparatus according to claim 1, in which the β-alumina is a β-alumina of lithium, sodium, potassium, rubidium, copper, silver, thallium, indium or gallium.

3. An apparatus according to claim 1, in which the tube of refractory material consists of α-alumina.

4. An apparatus according to claim 3, in which the pellet has a diameter from about ⅛ of an inch to about ¼ of an inch.

5. An apparatus according to claim 1, in which the pellet is formed in situ in the end of the tube by hot pressing of powder comprising β-alumina.

6. An apparatus according to claim 5, produced by hot pressing of powder comprising β-alumina at pressures of from about 20 up to about 100 Kg/cm² and at temperatures from about 1,000° to about 1,500° C.

7. An apparatus according to claim 6, produced by hot pressing of powder comprising β-alumina, both the pressure and the temperature having been increased during the hot pressing.

8. An apparatus according to claim 1, in which the electrodes are in the form of wires of a metal solid at 750° C.

9. An apparatus according to claim 1, in which the solid electrolyte comprises sodium β-alumina having a composition in the range from $Na_2O\cdot 5Al_2O_3$ to $Na_2O\cdot 11Al_2O_3$.

10. An apparatus according to claim 1, in which the solid electrolyte consists of a mixture of sodium β-alumina and α-alumina in which the ratio of $Na_2O$ to $Al_2O_3$ is in the range from about 1:11 up to about 1:12.

11. An apparatus for use in the detection or determination of an element in a substance containing said element, comprising:
    a voltmeter;
    an electrode directly contactable with the substance to be detected or determined, the electrode connected to one side of a voltmeter,
    a reference electrode connected to the other side of said voltmeter;
    a solid powdered reference material in contact with the reference electrode;
    a tube of refractory material containing the reference electrode and the powdered reference material;
    a solid electrolyte pellet contained in and sealing one end of the tube, said pellet being exposed for contact with the sample substance and consisting essentially of the β-alumina of lithium, sodium, potassium, rubidium, copper, silver, thallium, indium or gallium, and in contact with the reference electrode;
    the reference material being a compound of said element to be determined or detected which compound is solid at about 750° C. and is selected from the group consisting of two-phase β-alumina, a mixture of α-alumina and β-alumina, a tungstate, a molybdate and a vanadate;
    the tube, including the reference electrode, powdered reference material and pellet, being dippable into the substance containing the element to be detected or determined.

12. An apparatus according to claim 11, wherein the solid electrolyte comprises sodium β-alumina.

13. An apparatus according to claim 12, wherein the sodium β-alumina has a composition in the range of $Na_2O\cdot 5Al_2O_3$ to $Na_2O\cdot 11Al_2O_3$.

14. An apparatus according to claim 11 wherein α-alumina is the refractory material forming said tube.

* * * * *